US008367127B2

(12) United States Patent
Moriguchi et al.

(10) Patent No.: US 8,367,127 B2
(45) Date of Patent: Feb. 5, 2013

(54) TEA BEVERAGES CONTAINING PROANTHOCYANIDINS (75) Inventors: Shigeo Moriguchi, Tokyo (JP); Yuko Fukui, Osaka (JP); Mitsuhiro Zeida, Kawasaki (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 850 days.

(21) Appl. No.: 12/301,404

(22) PCT Filed: May 18, 2007

(86) PCT No.: PCT/JP2007/060276
§ 371 (c)(1),
(2), (4) Date: Nov. 18, 2008

(87) PCT Pub. No.: WO2007/136015
PCT Pub. Date: Nov. 29, 2007

(65) Prior Publication Data
US 2009/0186936 A1 Jul. 23, 2009

(30) Foreign Application Priority Data
May 19, 2006 (JP) ................................. 2006-140670

(51) Int. Cl.
A61K 36/82 (2006.01)
A61K 36/00 (2006.01)
(52) U.S. Cl. ........................................ 424/729; 424/725
(58) Field of Classification Search ........................ None
See application file for complete search history.

(56) References Cited

U.S. PATENT DOCUMENTS

| | | | |
|---|---|---|---|
| 3,436,407 A | 4/1969 | Masquelier | |
| 4,698,360 A | 10/1987 | Masquelier | |
| 5,968,517 A * | 10/1999 | Duncan et al. | 424/770 |
| 2005/0158409 A1 | 7/2005 | Takagaki | |
| 2007/0099853 A1* | 5/2007 | Iino et al. | 514/27 |
| 2007/0105837 A1* | 5/2007 | Czollner et al. | 514/215 |
| 2008/0026086 A1* | 1/2008 | Holyoak et al. | 424/770 |
| 2008/0124415 A1 | 5/2008 | Tanaka | |

FOREIGN PATENT DOCUMENTS

| | | | |
|---|---|---|---|
| CN | 1440666 A | * | 9/2003 |
| CN | 1545896 A | * | 11/2004 |
| EP | 0 713 706 | | 5/1996 |
| EP | 0 800 827 | | 10/1997 |
| EP | 1 547 591 | | 6/2005 |
| EP | 1 767 203 | | 3/2007 |
| JP | 08225453 A | | 9/1996 |
| JP | 2003061581 A | * | 3/2003 |
| JP | 2005021098 | * | 1/2005 |
| JP | 2005097324 A | | 4/2005 |
| JP | 2006038763 A | | 2/2006 |
| WO | WO-2004/010991 A | | 2/2004 |
| WO | WO-2006003909 A1 | | 1/2006 |

OTHER PUBLICATIONS

Extended European Search Report dated Sep. 23, 2010, for European Patent Application No. 07743711.9; 8 pages.
Moriguchi, S. et al., "The effect and safety of the tea beverage containing pine bark extract on endothelial function in humans", Yakuri to Chiryo—Japanese Pharmacology and Therapeutics, Raifu Saiensu Shuppan, Tokyo, JP, vol. 34, No. 5, Jan. 1, 2006, pp. 511-528, XP009132267 (partial translation).
Rhodewald, P., "A review of the French maritime pine bark extract (Pycnogenol®), a herbal medication with a diverse clinical pharmacology", International Journal of Clinical Pharmacology and Thereapeutics, Dustri-Verlag, Deisenhofen-Muenchen, DE, vol. 40, No. 4, Apr. 1, 2002, pp. 158-168, XP009027806.
Luximon-Ramma et al., "Characterization of the antioxidant functions of flavonoids and proanthocyanidins in Mauritian black teas," Food Research International, vol. 38, 2005, pp. 357-367, Elsevier.
International Search Report mailed Aug. 21, 2007 in International PCT Application No. PCT/JP2007/060276 filed May 18, 2007.
Mori et al., "France Kaigan Matsu Polyphenol 'Flavangenol' no Kasanka Kassei," New Food Industry, 2004, vol. 46, No. 5, pp. 1-7 (partial English-language translation).
Nakayama et al., "Biyo to Flavangenol," New Food Industry, 2005, vol. 47, No. 1, pp. 3-14 (partial English-language translation).
Matthews et al., "Extractable and Non-Extractable Proanthocyanidins in Barks," Phytochemistry, vol. 45, No. 2, pp. 405-410, 1997, Pergamon Press, New York, New York.
Verma et al., "Fundamentals of Endothelial Function for the Clinical Cardiolgist," Circulation, 2002, vol. 105, pp. 546-549, Lippincott Williams & Wilkins, Hagerstown, MD.
Shand et al., "Pilot Study on the Clinical Effects of Dietary Supplementation with Enzogenol®, A Flavonoid Extract of Pine Bark and Vitamin C," Phytotherapy Research, vol. 17, 2003, pp. 490-494.
Stein et al., "Purple Grape Juice Improves Endothelial Function and Reduces the Susceptibility of LDL Cholesterol to Oxidation in Patients with Coronary Artery Disease," Circulation, 1999, vol. 100, pp. 1050-1055, Lippincott Williams & Wilkins, Hagerstown, MD.
Chou et al., "Effect of Ingestion of Purple Grape Juice on Endothelial Function in Patients with Coronary Heart Disease," The American Journal of Cardiology, vol. 88, Sep. 1, 2001, pp. 553-555.
Agewall et al., "Does a glass of red wine improve endothelial function?" European Heart Journal, 2000, vol. 21, pp. 74-78.

(Continued)

Primary Examiner — Christopher R Tate
Assistant Examiner — Randall Winston
(74) Attorney, Agent, or Firm — Drinker Biddle & Reath LLP (57) ABSTRACT The object is to provide beverages that allow for sustained intake and which have an effect of improving the vascular endothelial function as by promoting the secretion of NO from vascular endothelial cells so as to potentiate the NO action.
The object is attained by providing proanthocyanidins containing tea beverages that contain procyanidin B1 (PB1) and procyanidin B3 (PB3) in a total amount not smaller than a certain concentration and which are free from any peculiar flavor to become easier to drink; they allow for sustained intake and have an effect of improving the vascular endothelial function.

12 Claims, 3 Drawing Sheets

OTHER PUBLICATIONS

International Search Report mailed on Aug. 21, 2007 in PCT/JP2007/060276 filed May 18, 2007.

Young et al., "Comparative effects of enzogenol® and vitamin C supplementation versus vitamin C alone on endothelial function and biochemical markers of oxidative stress and inflammation in chronic smokers," Free Radical Research, Jan. 2006, vol. 40, No. 1, pp. 85-94.

Supplementary European Search Report dated Sep. 23, 2010, issued in EP 07 74 3711.9.

Odom, "Camellia Sinensis—The Tea Plant," The Camellia Journal, Jun.-Aug. 2007, pp. 18-20.

European Search Opinion issued in European Application No. 07 743 711.9 dated Sep. 23, 2010.

Mori, Asami et al. "Intravenously Administered Vasodilatory Prostaglandins Increase Retinal and Choroidal Blood Flow in Rats," J. Pharmacol. Sci., 103, 103-112 (2007).

* cited by examiner

Comparison with placebo: + P<0.1; # p<0.05
(multiple comparison test by the Dunnett method)

TEA BEVERAGES CONTAINING PROANTHOCYANIDINS

CROSS REFERENCE TO RELATED APPLICATIONS

This application is the National Stage of International Application No. PCT/JP2007/060276, filed May 18, 2007, and claims benefit of Japanese Application No. 2006-140670, filed May 19, 2006, both of which are herein incorporated by reference in their entirety.

TECHNICAL FIELD

The present invention relates to the provision of foods containing clinically effective amounts of proanthocyanidins, in particular, to the provision of tea beverages that allow for efficient and sustained intake and which have a vascular endothelial function improving action.

BACKGROUND ART

In recent years, the incidence of lifestyle-related diseases is increasing among Japanese people on account of changes in their eating habit and lifestyle. Lifestyle-related diseases is the generic term for diseases including not only hypertension, hyperlipidemia and diabetes but also other diseases, such as angina pectoris, myocardial infarction, cerebral circulatory disturbance and malignant tumors, which might be prevented from manifestation by improving lifestyle. Diseases such as hypertension, hyperlipidemia and diabetes often develop in combination and if one disease is complicated by another, the morbidity of the respective diseases changes for the worse and sequelae such as arteriosclerosis are caused at high incidence, leading to poor prognosis.

Recently, it has been found that one of the factors involved in such vicious circle is vascular endothelial hypofunction (see Non-Patent Document 1). Risk factors in vascular endothelial hypofunction include hypertension, impaired glucose tolerance, hyperlipidemia, postmenopausal women, smoking, etc. and discovering and preventing the vascular endothelial hypofunction as a precursor of a vascular lesion before it causes arteriosclerosis in the terminal state is considered to be of utmost importance for the purpose of preventing lifestyle-related disease. In particular, as regards a vascular lesion that is a chronic asymptomatic disease, prevention by foods that can be ingested safely for a prolonged time is considered to be more important and the development of foods that exhibit such beneficial effect is being expected.

It has also been shown that the higher the intake of polyphenols, the lower the incidence of diseases in circulatory organs and recent studies have reported that foods and food ingredients such as cocoa, chocolate, grapes and wine that are rich in procyanidins as major polyphenols are effective in improving the vascular endothelial function in humans (see Non-patent Documents 2 to 4). It has also been verified that oral administration of capsules containing a pine bark extract containing procyanidins is effective in improving the vascular endothelial function (see Non-patent Documents 5 and 6).

[Non-patent Document 1] Verma S, Anderson T J, Circulation 2002; 105:546-549
[Non-patent Document 2] Stein J H, Circulation 1999; 100: 1050-5
[Non-patent Document 3] Chou E J, Am J Cardiol 2001; 88:553-5
[Non-patent Document 4] Agewall S, Eur Heart J 2000; 21:74-8
[Non-patent Document 5] Shand B, Phytother Res 2003; 17:490-4
[Non-patent Document 6] Young J M, Free Radic Res 2006; 40:85-94

DISCLOSURE OF THE INVENTION

Problems to be Solved by the Invention

The above-mentioned Non-patent Document 5 (Shand B, Phytother Res 2003; 17:490-4) describes the use of Enzogenol as a pine bark extract which, when continuously ingested for 12 weeks, increased the maximum forearm blood flow, thus showing a vascular endothelial function improving action, The above-mentioned Non-patent Document 6 (Young J M, Free Radic Res 2006; 40:85-94) also describes the use of Enzogenol as a pine bark extract which, when continuously ingested for 12 weeks, increased the blood vessel's diameter. In each of these documents, a solid composition for oral intake (capsule) was used and, what is more, the pine bark extract had to be ingested at a comparatively large dose of 480 mg/day, thus causing occasional inconvenience to daily intake. Generally speaking, solid compositions for oral intake take time to ingest and consumers may feel obliged to ingest them, and since the shapes of such solid compositions for oral intake which are typically in the form of tablets, capsules and granules are similar to those of pharmaceuticals, consumers may feel as they ingest pharmaceuticals; for these and other reasons, it has been pointed out that the shapes of beverages that can be casually taken in during meal or on a break are suitable as shapes that permit sustained ingestion. This is another reason why ingesting the above-described solid pine bark extracts in large amounts is not appropriate for sustained intake.

In addition, the beneficial effects described in those documents are not great enough to be reflected in biochemical examination of blood and they are yet to be demonstrated to have definite effectiveness.

An object, therefore, of the present invention is to provide beverages that allow for sustained intake and which have a definite effect of improving the vascular endothelial function as by promoting the secretion of NO from vascular endothelial cells so as to potentiate the NO action.

Means for Solving the Problems

The present inventors previously established a method of analyzing oligomeric proanthocyanidins and enabled quantitative measurement of proanthocyanidins in a pine bark extract (JP 2006-38763 A). It has been shown by this method of analysis that allegedly heat-stable proanthocyanidins are partly decomposed and/or isomerized by a sterilizing treatment to be reduced in content. From this observation, the present inventors assumed that the mere incorporation of the pine bark extract would not provide a clinically effective, blood flow improving composition and based on this assumption, they made intensive studies with a view to attaining the above-mentioned object; as a result, they have found that the sum of procyanidin B1 (PB1) and procyanidin B3 (PB3) can serve as an index for the content of proanthocyanidins. And it was found that when a proanthocyanidins containing tea beverage in which the sum of PB1 and PB3 was at least 6.4 mg/L, preferably at least 8.1 mg/L, was ingested continuously for 1-12 weeks at a daily dose of 350 mL, the vascular endothelial function was markedly improved. The following were also found from organoleptic evaluation: preferred proanthocyanidins containing tea beverages are such that the sum of PB1 and PB3 is no more than 30 mg/L, preferably no more than 20 mg/L; compared with an ethanol extracted pine bark, a pine bark extract obtained by extraction with hot water contained smaller amounts of phenylpropanoids, such as ferulic acid, and dihydroflavonols such as dihydroquercetin, making it extremely preferred in terms of taste and aroma. The present invention has been accomplished on the basis of these findings.

In summary, the present invention provides the following.

1. A proanthocyanidins containing tea beverage that contains procyanidin B1 (PB1) represented by formula (I):

[Formula 1]

(I)

and procyanidin B3 (PB3) represented by formula (II):

[Formula 2]

(II)

with their sum being at least 6.4 mg/L.

2. The tea beverage according to 1 above, wherein the PB1 and PB3 have been added as contained in a pine bark extract.

3. The tea beverage according to 2 above, wherein the pine bark extract is pine bark as extracted with hot water.

4. A tea beverage according to any one of 1 to 3 above and packed in a container, which is produced via a blending step of blending a liquid tea extract with proanthocyanidins to prepare a mixed solution, a sterilizing step of subjecting the mixed solution to a sterilizing treatment, and a filling step of filling the sterilized mixed solution into a container.

5. The tea beverage according to any one of 1 to 4 above, which has an action of improving the vascular endothelial function.

Effect of the Invention

The present invention provides tea beverages that contain procyanidin B1 (PB1) and procyanidin B3 (PB3) in a total amount of at least 6.4 mg/L, preferably at least 8.1 mg/L, with the sum of PB1 and PB3 being an index for the active ingredients. Simply ingesting the tea beverage at a dose of 350 mL per day contributes to improving the vascular endothelial function as by enhancing NO production and this results in prevention of arteriosclerosis and other diseases in circulatory organs.

PREFERRED MODE FOR CARRYING OUT THE INVENTION (Proanthocyanidins)

The tea beverages of the present invention contain proanthocyanidins, in particular, proanthocyanidins originating from pine bark, as active ingredients. Proanthocyanidins originating from the bark of pine trees can be obtained by extracting the bark of pine trees with hot water or solvents that are acceptable in food production (e.g. ethanol) or aqueous solutions thereof, each at 50-120° C., preferably at 70-100° C. (the former type of proanthocyanidins are hereinafter sometimes referred as "extracts with water" and the latter type which is obtained by extraction with ethanol or an aqueous solution of ethanol, as "extracts with ethanol"). The bark of pine trees that can preferably be used as the starting material for the pine bark extract may be derived from the following:

*Pinus Martima, Larix leptolepsis* (or *kaempferi*), *Pinus thunbergii, Pinus densiflora, Pinus parviflora* sieb. et zucc., *Pinus koraiensis, Pinus pumila, Pinus luchuensis, Pinus densiflora* form. *Umbraculifera, Pinus palustris, Pinus bungeana*, and the anneda in Quebec province, Canada. Among these, the bark of *Pinus Martima* is preferred. *Pinus Martima* is a maritime pine tree grown along a part of the Atlantic coast of southern France.

The bark of *Pinus Martima* contains various substances such as catechins, proanthocyanidins and organic acids. Its extract varies in composition with the extraction solvent used; for example, phenylpropanoids (PP) such as ferulic acid that are contained in the pine bark are hardly present in the extract with water but about 10% is contained in the extract with ethanol. In addition, dihydroflavonols (DHF) such as dihydroquercetin are hardly present in the extract with water but about a few percent is contained in the extract with ethanol. Ferulic acid and dihydroquercetin are known as powerful antioxidants and it has been reported that ferulic acid has a cerebrovascular protective action (Program A5 for Abstracts of Papers Read at the 14th Conference of the Japanese Association of Cardiovascular Pharmacology, 2004) and a vascular endothelial function improving action (see JP 2003-261444 A). Therefore, using the extract with ethanol, one can expect that proanthocyanidins and ferulic acid and/or dihydroquercetin will produce an additive or synergistic effect of improving the vascular endothelial function; on the other hand, the above-mentioned PP and DHF may have adverse effects on taste and aroma and, particularly in the case of beverages that are envisaged by the present invention where taste and aroma are important factors for sustained intake, those effects cannot be disregarded. In organoleptic tests, tea beverages to which the extract with water had been added were evaluated to have better flavor than ones to which the extract with ethanol had been added and, hence, the extract with water is preferably used in the tea beverages of the present invention. Specifically, with ferulic acid and dihydroquercetin being used as indices, it is preferred to use an extract in which the sum of their contents is not greater than 10 µm/mg, more preferably not greater than 5 µm/mg.

The contents of ferulic acid and dihydroquercetin in the pine bark extract can be analyzed by using, for example, HPLC as described below. The pine bark extract is concentrated in a buffer solution of pH 4 to 5 at a concentration of 1 mg/mL and, following the addition of β-glucosidase (e.g., cellulase RS or emulsion), the solution is incubated at 40° C. for 1-6 hours to form aglycon. To this aglycon-containing reaction mixture, an equal amount of acetonitrile (containing 0.1-1% TFA) is added so that not only is the enzymatic reaction quenched but also the aglycon is dissolved. The resulting solution is analyzed by reverse-phase HPLC to permit quantification.

(Conditions for HPLC)
  Column: Shim-pack FC-ODS, 4.6 mm×150 mm
  Mobile phase: A, 0.1% TFA/$H_2O$: B, 0.1% TFA/90% $CH_3CN$; 0.6 ml/min
  Gradient: B 20%→B 70% (10 min); B 70% iso (5 min)
  Detection: Photodiode array detector (SPD-M10A of Shimadzu Corporation); A 330 nm
  Injection: 10 µl.

Aside from those mentioned above, HPLC may use carriers such as ODS and C30 so long as a reverse-phase system can be realized.

The method of extraction from the bark of pine trees is not limited in any particular way and known methods, including heated extraction, supercritical fluid extraction, liquid carbon dioxide batch process, liquid carbon nitrogen refluxing, and supercritical carbon dioxide refluxing, may be used either individually or in combination of two or more.

In the present invention, the bark of pine tree as extracted in the presence of an added extraction solvent (e.g. hot water, ethanol, or aqueous ethanol) may be filtered to give a filtrate which, in turn, may be purified; either the filtrate or its purified product may also be used as a liquid extract; the liquid extract may be freeze-dried or otherwise processed to form a powder. Commercial products of pine bark extract, such as Flavangenol (TOYO SHINYAKU Co., Ltd.) and Pycnogenol (Siber Hegner A G.), may also be used; among others, Flavangenol of a water extracted type can be used with advantage for the reason mentioned above.

The proanthocyanidins as referred to in the present invention are a group of compounds that comprise condensed polymers of flavan-3-ol and/or flavan-3,4-diol as building composition that have polymerization degrees of at least two. Known proanthocyanidins in the bark of pine tree include dimers such as PB1, PB3 and PB6, and trimers such as procyanidin C2 (C—C—C). Proanthocyanidins extracted from grape seeds are known to be heat stable (Japanese Patent No. 2694748); however, in the tea beverages of the present invention, particularly those which are to be sold after being heat sterilized and put into containers, the sterilizing treatment at temperatures in excess of 120° C. causes proanthocyanidins as the active ingredient to be partly decomposed or isomerized and, hence, the proanthocyanidins in the pine bark extract before heating (sterilizing treatment) and the proanthocyanidins in the pine bark extract after heating (sterilizing treatment) may sometimes differ in content and composition. The tea beverages of the present invention are characterized by containing clinically effective amounts of proanthocyanidins. As mentioned above, proanthocyanidins may occasionally be decomposed, typically by the sterilizing treatment in the process of beverage production and to know their contents, the sum of procyanidin B1 (PB1) that is represented by formula (I):

[Formula 3]

(I)

and procyanidin B3 (PB3) that is represented by formula (II):

[Formula 4]

(II)

can be used as an index. With the tea beverages of the present invention which have a vascular endothelial function improving action, the sum of the above-mentioned PB1 and PB3 is preferably used as an index for choosing and adjusting the types and the amounts of addition of proanthocyanidins or plant extracts containing the same.

The present invention provides tea beverages which, with PB1 and PB3 being used as an index, contains at least 2.2 mg, preferably at least 2.8 mg, per adult (weighing 60 kg) daily. For example, a tea beverage incorporating a pine bark extract that has been produced in a 350-mL container to contain PB1 and PB3 in a total amount of 2.2 mg (preferably 2.8 mg) needs to be drunk in a volume as small as one pack a day (350 mL) and yet the action of improving the vascular endothelial function can be obtained.

Thus, the present invention has the advantage that by ingesting proanthocyanidins as a tea beverage, it needs to be drunk in only a small amount and yet a definite effect is exhibited. The upper limit of the proanthocyanidins that can be incorporated in the tea beverages of the present invention is substantially absent; however, since there is no marked relationship between the amount of proanthocyanidins incorporated and the magnitude of their effect (see FIGS. 4 and 6), they may be incorporated in clinically effective amounts considering economy. If the bark of pine tree is used as proanthocyanidins, a beverage incorporating it in an unduly large amount will feel pungent or exhibit some other peculiar taste or aroma and becomes difficult to drink; hence, the bark of pine tree as proanthocyanidins is preferably not incorporated in unduly large amounts and, specifically, with the total content of PB1 and PB3 taken as an index, it is preferably contained in an amount not greater than 30 mg/L, more preferably not greater than 20 mg/L.

The contents of PB1 and PB3 in the tea beverages of the present invention can typically be measured as follows. First, the tea beverage is subjected to a preliminary treatment as on a column. The column can be exemplified by Sephadex LH-20. The column packed with Sephadex LH-20 and later swollen with water is loaded with the tea beverage and after washing with water, the column is eluted with 35% ethanol and 70% ethanol. After concentrating the 70% ethanol eluted fraction under reduced pressure, the concentrate is filled up in a measuring flask and the respective eluted fractions are subjected to HPLC.

(Conditions for HPLC)
Column: Cosmosil 5C18-MS-II, 5 µm, 4.6 mmφ×150 mm
Mobile phase: A, 0.05% TFA/$H_2O$; B, 90% $CH_3CN$/0.05% TFA/$H_2O$; 1 ml/min
Gradient program: 9% B isocratic (15 min), 9% B→100% B (1 min), 100% B isocratic (10 min), 100% B→9% B (1 min), and 10 min equilibration for starting the next analysis
Detection: A 225 nm
Injection: 10 µL.

(Process for Producing Tea Beverages)

The tea beverages of the present invention are prepared by adding proanthocyanidins comprising PB1 and PB3, preferably a plant extract containing proanthocyanidins, to a liquid tea extract. The liquid tea extract is obtained by extracting tea leaves as a starting material with heated water and removing the extraction residue from the resulting liquid tea extract. Tea leaves that may be used as the starting material in the present invention are not limited in any particular way and may include: green teas such as sencha, gyokuro, and tencha; semi-fermented teas collectively referred to as oolong teas such as tie quan yin, shikishu, and huang jin gui; fermented teas called black teas such as Darjeeling tea, Assam tea, and Sri Lanka tea; as well as housyucha, pine leaf tea, barley tea, and blended teas; among these, green teas and housyucha are used with advantage because of preference in terms of flavor. In addition, the variety of tea leaves, place of their production, the time of harvesting, method of harvesting, method of cultivation, and other factors are in no way limited and any tea leaves, such as raw tea leaves (including foliage and stems), can be used as the starting tea leaves. Extraction can be performed by known methods using an extracting apparatus such as a kneader. Specifically, the starting tea leaves are extracted with 20-100 volumes of extracting water at 70-100° C. (preferably 70-90° C.) for about one minute to 20 minutes, optionally with stirring once or several times, under atmospheric or super-atmospheric pressure. The extracting water to be used here may be exemplified by not only pure water (including hard water, soft water, or ion-exchanged water) but also an aqueous solution containing ascorbic acid, water with adjusted pH, etc.

The liquid tea extract obtained by extracting the starting tea leaves is then filtered or otherwise treated to remove the extraction residue and optionally centrifuged or otherwise treated to remove the fines. The conditions for centrifugation (e.g. the flow rate and the number of revolutions) may be chosen as appropriate by considering such factors as the clarity of the tea beverage to be finally obtained. During centrifugation, the liquid extract is preferably cooled to about 5-40° C. Centrifuging under cooled conditions contributes to increasing the clarity of the tea beverage to be finally obtained.

To produce the tea beverage of the present invention, proanthocyanidins or a plant extract containing them is added to, and dissolved with mixing, in the above-described liquid tea extract from which the extraction residue has been removed (the blending step). The tea beverage of the present invention is characterized by containing a clinically effective amount of proanthocyanidins and their content is at least 6.4 mg/L, preferably at least 8.1 mg/L, with the total content of PB1 and PB3 being taken as an index. Considering the decomposition and/or epimerization of proanthocyanidins by a sterilizing treatment, proanthocyanidins are added in the blending step in larger amounts than are necessary to obtain the desired content.

In addition, the tea beverage of the present invention may optionally get ascorbic acid, sodium ascorbate, sodium hydrogencarbonate and the like to be added for various purposes such as pH adjustment to somewhere around 6.0, concentration adjustment, and taste adjustment. The addition of ascorbic acid can not only prevent the oxidation of the extracted tea component in the tea beverage but also the antioxidizing action of the ascorbic acid can be anticipated to combine with the proanthocyanidins of the present invention either additively or synergistically to exhibit an enhanced vascular endothelial function improving action.

The tea beverages of the present invention can advantageously be offered as container packed beverages. The term "container packed beverages" as used hereinabove refers to beverages that are accommodated in containers such as PET containers, cans, bottles and paper containers and which can be drunk without being diluted. The container packed beverages are usually manufactured by performing a heat sterilizing treatment on the mixed solution obtained in the blending step and filling it into a container. The heat sterilizing treatment may be any of the treatments prescribed in the Food Sanitation Law; in the case of a canned beverage, hot packing is followed by filling and sterilizing in a retort (as by heat sterilization at 121° C. for 7 minutes under an appropriate super-atmospheric pressure (say, 1.2 mmHg)); in the case of a plastic bottled beverage, UHT sterilization may be performed (by holding the mixed solution at 120-150° C. for one second to several tens of seconds).

As already mentioned above, the tea beverages of the present invention are manufactured via the extracting step of extracting tea leaves with heated water, the step of removing the extraction residue from the liquid tea extract, the blending step of mixing the liquid tea extract with proanthocyanidins, a plant containing them, or the like to prepare a mixed solution, appropriately followed by the sterilizing step and the container filling step. Note that these production steps are only mentioned for illustrative purposes. The order of individual steps may be reversed or they may be separated by another step.

(Vascular Endothelial Function Improving Action)

The vascular endothelium is not just the tissue of a surface layer that lines the lumina of blood vessels; it also plays an important role in maintaining the homeostasis of blood vessels. The vascular endothelial function can be evaluated using flow-mediated dilation (FMD). A method commonly employed for experimental determination of FMD is to measure the reactive hyperemic arterial flow and the resting basal blood flow by plethysmography. This method consists of first measuring the basal blood flow at rest, then avascularizing the forearm, ceasing the avascularization and measuring the resulting change in the blood flow (reactive hyperemic arterial flow) per unit muscular tissue (100 mL); items to be evaluated may include (1) AUC (area under the curve) of the blood flow after cessation of avascularization (AUC for the ratio of the reactive hyperemic arterial blood flow to the resting arterial inflow), (2) a maximum blood flow after cessation of avascularization, and (3) the blood flow measured 30-60 seconds after cessation of avascularization (J. Pharmacol Sci. 2003; 93:399-404). The proanthocyanidins containing tea beverage of the present invention, if taken by sustained ingestion (continued intake for 1-12 weeks), causes an increase in the AUC of the blood flow after cessation of avascularization, an increase in the maximum blood flow after cessation of avascularization, and an increase in the blood flow measured 45 seconds after cessation of avascularization and may, hence, be described as having a superior vascular endothelial function improving action.

The vascular endothelial function can also be evaluated by a hematological test. It is known that endothelial cells found in the innermost part of blood vessels secrete various physiologically active substances typified by nitrogen monoxide (NO). Therefore, the vascular endothelial function can be evaluated by measuring the amount of NO closely associated with this vascular endothelial function. Since NO is oxidized soon after it was secreted from vascular endothelial cells, the measurement of NO instead depends on its metabolites such as $NO_2^-$, nitrosothiol, and NOx. In continued intake trials, epidemiological investigations and the like, NOx which is the sum of $NO_2^-$ and $NO_3^-$ is used and it has been reported that hypertensive persons and smokers experience lowered blood NOx levels. The proanthocyanidins containing tea beverage of the present invention, if taken by sustained ingestion for 4-12 weeks, causes an increase in the blood NOx and may, hence, be described as having a NO-dependent, vascular endothelial function improving action.

As described above, the tea beverages of the present invention have a vascular endothelial function improving action. Therefore, they can be used advantageously in persons who are deteriorated in the vascular endothelial function (persons suffering from or prone to arteriosclerosis) but they are expected to show their preventive efficacy if drunk by healthy persons. The relative increase in the arterial blood flow, or the reactive hyperemic arterial blood flow that is divided by the resting basal blood flow, generally presents a maximum value of more than 400 in healthy persons whereas people who are deteriorated in the vascular endothelial function are said to have this value in the range from 0 (inclusive) to 400 (inclusive). The present invention is primarily intended to be applied to persons who have a maximum value of the relative increase in the arterial blood flow in the range from 0 (inclusive) to 400 (inclusive).

EXAMPLES

On the following pages, the present invention is described with reference to working examples and tests but it should be understood that the present invention is by no means limited to those working examples and tests.

[Test 1] Vascular Endothelial Function Improving Action (In Vivo Evaluation)

1. Preparing Proanthocyanidins-Rich Fraction (PF, or Procyanidin Fraction)

Flavangenol (TOYO SHINYAKU Co., Ltd.: Lot. T-0027) was used as a pine bark extract (PBE). This pine bark extract was passed through separating and purifying steps to prepare a procyanidin fraction (PF). To be more specific, 7.5 g of the pine bark extract was dissolved in 30 ml of 10% EtOH, loaded on a column of Sephadex LH-20 resin (Amersham Pharmacia), which was eluted successively with 3 L of $H_2O$ and 3 L of 35% EtOH; thereafter, four fractions of 70% EtOH, each weighing 1.5 L, were flowed and the resulting 2-4 fractions eluted with 70% EtOH were combined, concentrated under reduced pressure, and freeze-dried to prepare a procyanidin fraction (PF). The LH-20 column had been washed with 1.5 L of 50% acetone and equilibrated with 4.5 L of water before use.

2. Evaluating the Function of Blood Vessels (by Animal Test)

Cr1:CD (SD) male rats were purchased from CHARLES RIVER LABORATORIES JAPAN, INC. and after acclimatization for a certain period, they were subjected to an experiment at 20-21 weeks. The animals were kept in an air-conditioned cage (SPF; temperature, 23.5±1.0° C.; humidity, 55±10%; frequency of ventilation, 12-15 times/hour; illumination, 7:00-19:00/day). Throughout the period of acclimatization, the animals were allowed to ingest a commercial feed (CE-2, CLEA Japan, Inc.) and tap water ad libitum.

After fasting overnight, 16 rats were divided into three groups, a water administered group (control), a pine bark extract administered group (PBE) and a procyanidin fraction administered group (PF), and solutions of the respective test samples were forcibly administered by oral route in an amount of 5 ml/kg. The pine bark extract was administered at a dose of 150 mg/kg on a dry weight basis whereas the procyanidin fraction was administered at a dose of 120 mg/kg on a dry weight basis; the amount of procyanidin for the PBE and that for the PF were set to be almost comparable by computation based on the analytical values listed below under "3. Compositional analysis of the pine bark extract."

One hour after the administration of the solutions of test samples, the rats were administered intraperitoneally with 0.08 ml/kg of the analgesic Nembutal and thereafter subjected to an experiment on a heater mat (KN-210-5, NATSUME SEISAKUSHO CO., LTD.) that had been set at 37° C. (the laboratory's temperature was set at about 23° C.). A cuff (DC1.6, D. E. Hokanson, Inc.) was placed in the basal portion of the tail and with a mercury strain gage (6.0 cm, D. E. Hokanson, Inc.) being wrapped around a terminal site 2-4 cm distant from the cuff, the arterial inflow was measured using a plethysmograph (EC6, D. E. Hokanson, Inc.) After more than six measurements of the arterial inflow at rest, the cuff wrapped around the basal portion of the tail was inflated to a pressure of 300 mmHg and avascularization was effected for 3 minutes. At zero seconds after the reactive hyperemia, the arterial inflow was measured 15 times at intervals of 20 seconds. The obtained results of measurements were analyzed using a noninvasive vascular analyzing system (NIVP3, D. E. Hokanson, Inc.)

Figure 1:
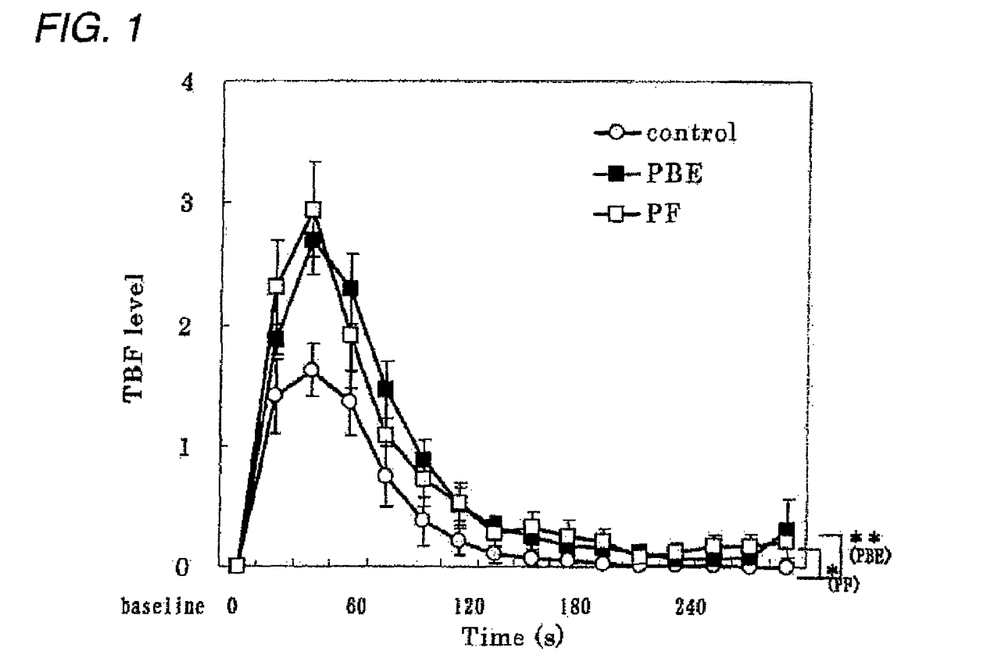
FIG. 1 is a graph showing the changes with time in the ratio of the arterial inflow after reactive hyperemia to the arterial inflow at rest (TBF level, or tail blood flow level) in rats administered with test beverages of the present invention; in the graph, PBE refers to the group treated with a pine bark extract and PF to the group treated with a procyanidins-rich fraction.
Figure 2:
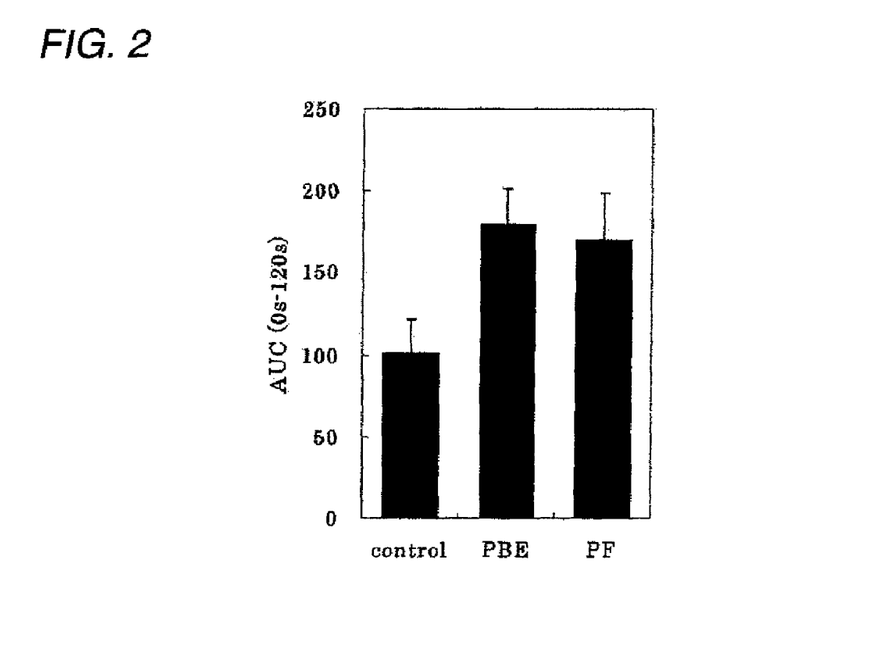
FIG. 2 is a graph showing the area under the curve (AUC) for the ratio of the arterial inflow from zero to 120 seconds after reactive hyperemia to the arterial inflow at rest in rats administered with test beverages of the present invention.

No significant difference in the arterial inflow at rest was recognized between groups. The ratio of the arterial inflow after reactive hyperemia to the arterial inflow at rest (TBF level, or tail blood flow level) was computed and the baseline was corrected to zero. The results obtained are shown in FIG. 1. Each of the PBE and PF showed higher values than the control, revealing the vascular endothelial function improving action. The AUC (area under the curve) for the ratio of the arterial inflow for 0-120 seconds of reactive hyperemia to the arterial inflow at rest was investigated and the result is shown in FIG. 2. Again, each of the PBE and PF showed higher values than the control. This also revealed the vascular endothelial function improving action.

Prom the foregoing, it was suggested that the substance in the pine bark extract that played part in the vascular endothelial function improving action would be proanthocyanidins.

3. Compositional Analysis of the Pine Bark Extract

The pine bark extract and the procyanidin fraction that were used in the animal tests were analyzed for their composition. Specifically, the following five contents were measured; catechin and epicatechin (C+EC); proanthocyanidins (Pr); phenylpropanoids (PP); dihydroflavonols (DHF); and others. The respective contents were analyzed by the following methods.

3.1 C+EC

The pine bark extract (2 mg) was dissolved in 10 mL of 10% ethanol and after passing the solution through a 0.45 μm filter, the filtrate was subjected to HPLC (Shimadzu Corporation, LC-10A System/S PD-10Avp detector) under the following conditions. From the results of HPLC measurement, the catechins in the samples were quantified using calibration curves constructed with 10% ethanol solutions of (+)-catechin and (-)-epicatechin in amounts of 50 μg/mL and 10 μg/mL. For the quantification, area values at A 225 nm were used. Under the conditions employed, the elution time for (+)-catechin and (-)-epicatechin was 8.1 min and 9.5 min.

(Conditions for HPLC)
Column: Cosmosil 5C18-MS-II, 5 μm, 4.6 mmφ×150 mm (nacalai tesque)
Mobile phase: A, 0.05% TFA/$H_2O$; B, 90% $CH_3CN$/0.05% TFA/$H_2O$; 1 ml/min
Gradient program: 9% B isocratic (15 min), 9% B→100% B (1 min), 100% B isocratic (10 min), 100% B→9% B (1 min), and 10 min equilibration for starting the next analysis
Detection: A 225 nm
Injection; 10 μL.

3.2 Pr

The pine bark extract (1 mg) was dissolved in 1 mL of 0.6N—HCl/butanol in a glass test tube and allowed to stand for 2 hours in a 90° C. hot water bath. After the end of the reaction, the solution was passed through a 0.45 μm filter and subjected to HPLC under the following conditions to quantitate anthocyanidins. As the standard substance for quantification, cyanidin (purchased from Funakoshi Corporation) was used. Since cyanidin eluted in 5.5 minutes and had $\lambda_{max}$ of 525 nm, the component that agreed with that data was quantified as cyanidin. As the standard substance for OPC, procyanidin B1 (Funakoshi Corporation) was subjected to the same reaction in an amount of 0.5 mg/mL and the amount of the resulting cyanidin was compared to determine the Pr content.

(Conditions for HPLC)
Column: YMC-ODS-A312, 6 mmφ×150 mm
Mobile phase: $CH_3COOH$:MeOH:$H_2O$=15:17.5:67.5
Detection: A 520 nm (for PDA, measurement was conducted at 400-600 nm)

3.3 PP

The pine bark extract was dissolved in an enzyme solution (0.06M sodium acetate buffered solution containing 0.5 mg/mL of cellulase RS (Yakult Honsha Co., Ltd.)) to give a final concentration of 0.5 mg/mL; the solution was incubated at 40° C. for 1.5 hours, diluted 2-fold with 0.1% TFA/$CH_3CN$, passed through a 0.45 μm filter, and subjected to HPLC under the following conditions. As the standard substance for quantification, ferulic acid (purchased from nacalai tesque) was used. Since ferulic acid eluted in 7.5 minutes and had $\lambda_{max}$ of 327 nm, the component that agreed with that data was quantified as ferulic acid. In addition, the p-coumaric acid and caffeic acid that had been determined by the same HPLC were combined to give the PP content.

(Conditions for HPLC)
Column: Shim-pack FC-ODS, 4.6 mm×150 mm
Mobile phase: A, 0.1% TFA/$H_2O$; B, 0.1% TFA/90% $CH_3CN$; 0.6 ml/min
Gradient: B20%→B70% (10 min), B70% iso (5 min)
Detection: Photodiode array detector (Shimadzu Corporation, SPD-M10A), A 330 nm
Injection: 10 μL 3.4 DHF Dihydroquercetin was quantified by performing HPLC as in the above-described case of PP, except that detection was conducted at A 280 nm. As the standard substance for quantification, dihydroquercetin (Trade name: taxifolin; purchased from Funakoshi Corporation) was used. Since dihydrokaempferol eluted in 7.2 minutes and had $\lambda_{max}$ of 286 nm, the component that agreed with that data was quantified as dihydroquercetin. In addition, the dihydroquercetin and dihydromyricetin that had been determined by the same HPLC were combined to give the DHF content.

The results of analyses are shown in Table 1. From the results of animal tests and analytical results, it was suggested that proanthocyanidins would be involved in the vascular endothelial function improving action.

TABLE 1

|  | C + EC | Pr | PP | DHF | (Unit: wt %) Others |
|---|---|---|---|---|---|
| PBE | 6 | 60 | 0.5 | 0.5 | 33 |
| PF | 12 | 75 | 0 | 0 | 13 |

Note that the amounts of PB1 and PB3 in PBE's proanthocyanidins and their sum were 39.3 mg/g, 19.7 mg/g and 59 mg/g, respectively, whereas the respective amounts in PF's proanthocyanidins were 102.9 mg/g, 58.7 mg/g and 161.6 mg/g (the methods of measurements were the same as in Example 1.)

Example 1

Vascular Endothelial Function Improving Action-1 of Proanthocyanidins Containing Tea Beverages in Human Volunteers 1. Production of Proanthocyanidins Containing Tea Beverages Eight kilograms of a mixture of green tea and houshoucha leaves was extracted for 5 minutes with 300 L of added warm water at about 80° C. and, following cooling to less than 30° C., the tea leaves were removed by centrifugation to yield a liquid tea extract. In accordance with the recipes shown in Table 2, a pine bark extract and L-ascorbic acid were mixed and dissolved in the liquid tea extract; thereafter, sodium hydrogencarbonate was added to yield mixed solutions with the pH adjusted to 6.0. Subsequently, the mixed solutions were subjected to degassing and sterilizing treatments (sterilizing conditions: 135° C.×30 seconds), filled into 350 mL PET bottles (ca. 80° C.), and cooled to prepare a total of four sample beverages, one control (P) and three test beverages (Q, R, S). It was confirmed that the sample beverages (P, Q, R, S) were indistinguishable from one another in terms of sensory stimulus (taste and aroma), appearance, and properties.

TABLE 2

|  | P (control) | Q | R | S |
|---|---|---|---|---|
| Liquid tea extract |  | 350 mL |  |  |
| Pine bark extract*[1] | 0 mg | 40 mg | 80 mg | 160 mg |
| L-ascorbic acid |  | 100 mg |  |  |

*[1]TOYO SHINYAKU Co., Ltd. (Flavangenol Lot. T-0030; water-extracted type)

2. Measuring PB1 and PB3 Contents

The four sample beverages (P, Q, R, S) were measured for the amounts of procyanidin B1 (PB1) and procyanidin B3 (PB3) by the following procedure.

First, the four sample beverages (P, Q, R, S) were subjected to a preliminary treatment with Sephadex LH-20. A column packed with the LH-20 (Amersham Bioscience) in a dry weight of 0.25 g and later swollen with water was loaded with 5 mL of a sample beverage, washed with 2 mL of water, and eluted with 2 mL of 35% EtOH and 4 mL of 70% EtOH. The fraction eluted with 70% EtOH was concentrated under reduced pressure, filled up in a 2-mL measuring flask, and passed through a 0.45 μm filter to make respective test solutions.

HPLC was conducted under the conditions set forth below to quantitate PB1. For qualitative determination, the test solutions were subjected to HPLC analysis under the same conditions as for the standard sample and the peak that agreed with the retention time for elution of the standard PB1 sample (6.3 minutes) and the peak that agreed with procyanidin B3 (PB3) having an elution time of 7.5 minutes were identified as PB1 and PB3, respectively, and the two were combined as procyanidins. In the quantitative test, the peak area was measured for the elution peak identified as PB1 and the content of PB1 in a test solution was computed from a calibration curve constructed on the basis of the peak area of the standard PB1 sample. To construct the calibration curve, the standard PB1 sample was dissolved in a 10% ethanol solution at concentrations of 2, 5, and 10 μg/mL to make standard solutions with the respective concentrations (prepared just before use) and each of the standard solutions was subjected to HPLC under the conditions set forth below; the calibration curve plots the PB1 concentration on the horizontal axis and the peak area on the vertical axis.

(Conditions for HPLC)
  Column: Cosmosil 5C18-MS-II (4.6φ×150 mm; product of nacalai tesque)
  Mobile phase: (Fluid A) acetonitrile-water (8:92) in 0.05% trifluoroacetic acid
    (Fluid B) acetonitrile-water (50:50) in 0.05% trifluoroacetic acid
  Flow rate: 1.0 ml/min
  Temperature: 40° C.
  Detection: UV absorption at 225 nm
  Injected dose: 10 μL
  Gradient program: See Table 3.

TABLE 3

|  | Time (min) | | | | | |
|---|---|---|---|---|---|---|
|  | 0 | 15 | 16 | 26 | 27 | 42 |
| Fluid A's concentration (%) | 100 | 100 | 0 | 0 | 100 | 100 |
| Fluid B's concentration (%) | 0 | 0 | 100 | 100 | 0 | 0 |

The results of measurements are shown in Table 4. When test beverage Q was not subjected to a sterilizing treatment, PB1 and PB3 were 1.84 and 3.29 mg/L, respectively, giving a total of 5.13 mg/L.

TABLE 4

|  | PB1 | PB3 | Total |
|---|---|---|---|
| P (pine bark extract: 0 mg) | 0.39 | 1.62 | 2.00 |
| Q (pine bark extract: 40 mg) | 1.96 | 2.80 | 4.76 |
| R (pine bark extract: 80 mg) | 3.40 | 4.70 | 8.10 |
| S (pine bark extract: 160 mg) | 7.25 | 8.51 | 15.76 |

(Unit: mg/L)

3. Evaluating Vascular Endothelial Function by Plethysmography

Twenty-one healthy male and female adults aged between 20 and 65 were chosen as volunteers after they gave informed prior consent to participating in the trial from ethical consideration; they were either men whose fasting blood glucose was found to be 110-139 mg/dL in a preliminary examination conducted two weeks before the trial, or men having a systolic blood pressure of 130-159 mmHg or a diastolic blood pressure of 85-99 mmHg, or postmenopausal women. These volunteers were randomly divided into four groups (n=4-6) and subjected to a one-week long, double-blind test by a crossover design. More specifically, the four groups of volunteers were asked to drink each of the four sample beverages (P, Q, R, S) in one pack (350 mL) per day for a period of one week.

To evaluate the vascular endothelial function, the reactive hyperemic arterial blood flow of each volunteer and his or her resting basal blood flow were measured by plethysmography (Plethysmograph EC6, Primetech Co.) To measure the resting basal blood flow, the volunteer stayed at rest by lying in a supine position for 30 minutes and, thereafter, three cuffs and a strain gage were wrapped around the arm which was not the preferred arm and the forearm arterial blood flow was measured at 15 minutes and thereafter. At least seven measurements were conducted and their results were processed to compute a trimmed mean of five measurements. The reactive hyperemic arterial blood flow was measured by the following procedure: after the measurement of the resting basal blood flow, the cuffs wrapped around the forearm were inflated to a blood flow divided by the resting basal blood flow (B/A), from those results of measurements.

As regards the resting basal blood flow (A), neither of the groups ingesting the test beverages (Q, R, S) showed any significant difference from the group ingesting the control (P) irrespective of whether the comparison was made before or after the ingestion; however, as regards the reactive hyperemic arterial blood flow (maximum forearm arterial blood flow after cessation of avascularization=blood flow at zero seconds after cessation of avascularization) (B) and the relative increase in arterial blood flow (B/A), the group ingesting the test beverage (R) containing 80 mg of the pine bark extract and the group ingesting the test beverage (S) containing 160 mg of the pine bark extract had significantly higher values than the group ingesting the control (P). Note here that since the healthy persons who volunteered in the present trial had maxima of the relative increase in the arterial blood flow (B/A) ranging from 190.1 to 1436.2, some of them might have been deteriorated in the vascular endothelial function. As a result of continued ingestion of the test beverages (Q, R, S), the volunteers got their relative increase in the arterial blood flow to shift to range from 235.4 to 2200.3.

TABLE 5

| | | Before ingestion | After ingestion | | |
|---|---|---|---|---|---|
| Resting basal blood flow A (ml/min/100 ml tissue) | P (pine bark extract: 0 mg) | 3.8 ± 1.0 | 3.4 ± 1.0 | | |
| | Q (pine bark extract: 40 mg) | 3.8 ± 1.1 | 3.4 ± 0.9 | | |
| | R (pine bark extract: 80 mg) | 3.7 ± 1.1 | 3.3 ± 0.7 | | |
| | S (pine bark extract: 160 mg) | 3.9 ± 1.3 | 3.4 ± 1.2 | | |
| Reactive hyperemic arterial blood flow B (ml/min/100 ml tissue) | P (pine bark extract: 0 mg) | 23.3 ± 9.5 | 21.6 ± 8.9 | | |
| | Q (pine bark extract: 40 mg) | 21.4 ± 9.7 | 20.4 ± 10.8 | ### | |
| | R (pine bark extract: 80 mg) | 22.7 ± 7.7 | 33.1 ± 10. | | ### |
| | S (pine bark extract: 160 mg) | 20.5 ± 7.1 | 31.1 ± 9.1 | | |
| Relative increase in arterial blood flow B/A (% FBF) | P (pine bark extract: 0 mg) | 663.9 ± 335.1 | 698.1 ± 366.3 | | |
| | Q (pine bark extract: 40 mg) | 601.5 ± 272.0 | 614.1 ± 319.8 | ## | |
| | R (pine bark extract: 80 mg) | 620.3 ± 196.4 | 1037.5 ± 431.5 | | ## |
| | S (pine bark extract: 160 mg) | 554.4 ± 187.6 | 983.5 ± 390.8 | | |

Values in the table are expressed in mean ± standard deviation.
Comparison with the group ingesting control (P)
: $p < 0.05$;
: $p < 0.01$:
: $p < 0.001$ (paired t test)

pressure at least 50 mmHg higher than the systolic blood pressure; following this avascularization for 5 minutes, the cuffs were deflated and starting at zero seconds, the forearm arterial blood flow was measured at intervals of 15 seconds.

Figure 3:
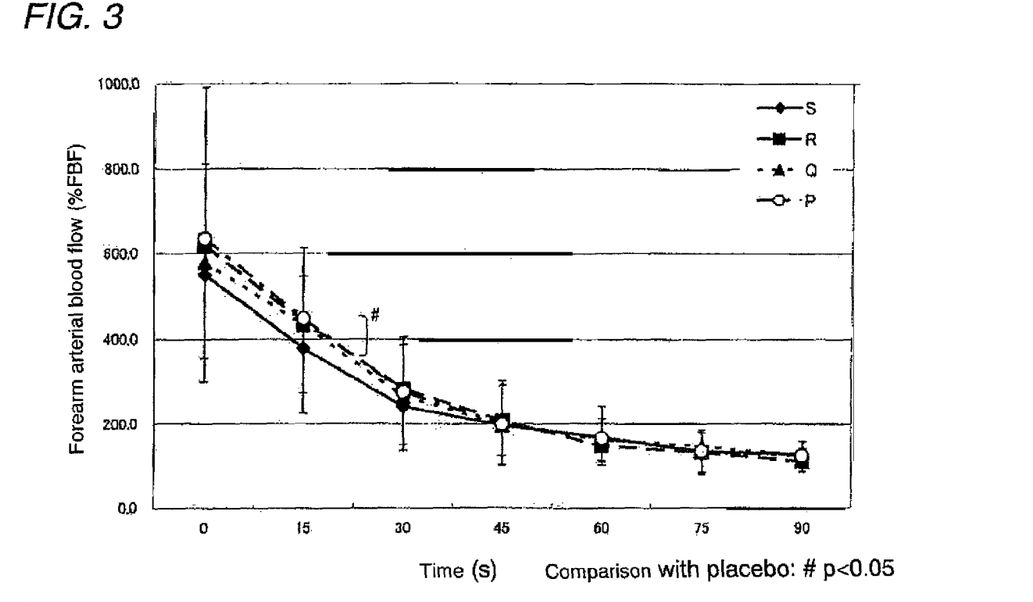
FIG. 3 is a graph showing the change with time in the relative increase of arterial blood flow (% FBF), or the reactive hyperemic arterial blood flow divided by the resting basal blood flow (B/A), in humans due to the ingestion of test beverages of the present invention.
Figure 4:
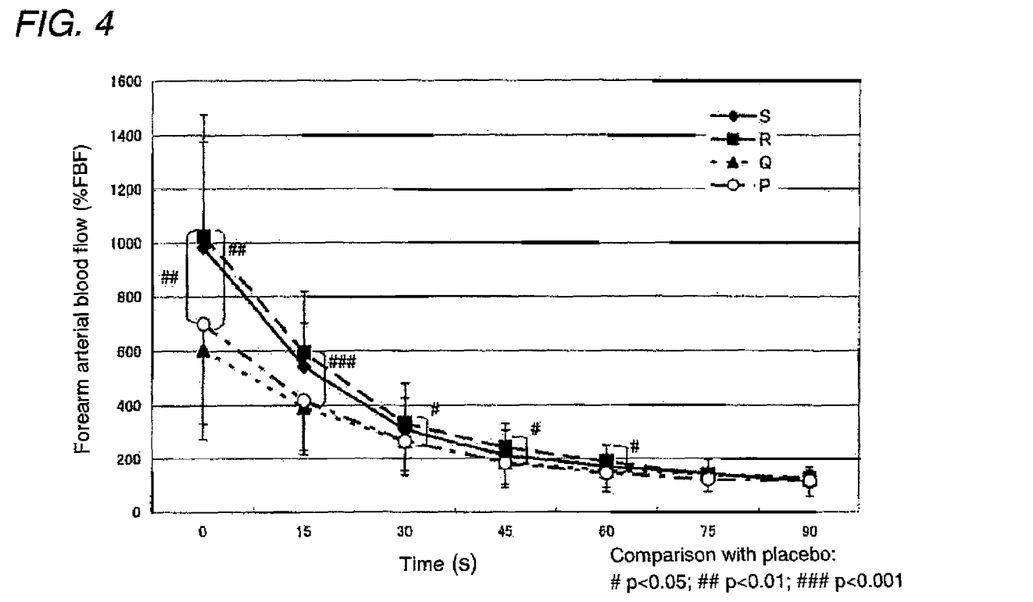
FIG. 4 is a graph showing the change with time in the relative increase of arterial blood flow (% FBF), or the reactive hyperemic arterial blood flow divided by the resting basal blood flow (B/A), in humans due to the ingestion of test beverages of the present invention.

FIGS. 3 and 4 show the changes with time in the relative increase of arterial blood flow (% FBF), or the reactive hyperemic arterial blood flow divided by the resting basal blood flow. Table 5 shows the results of measurements of the resting basal blood flow (resting forearm arterial blood flow) (A) and the reactive hyperemic arterial blood flow (maximum forearm arterial blood flow after ceasing avascularization) (B), as well as the results of computing the relative increase of arterial blood flow (% FBF), or the reactive hyperemic arterial The blood flow at 45 seconds after cessation of avascularization C was also analyzed. Table 6 shows the results for the blood flow at 45 seconds after cessation of avascularization C and the relative increase in the arterial blood flow as computed from C(C/A) (for the resting basal blood flow A, the values listed in Table 5 were adopted). As regards the blood flow at 45 seconds after cessation of avascularization (C) and the relative increase in the arterial blood flow (C/A), either of the groups ingesting the test beverages (Q, R, S) had higher values than the group ingesting the control (P) and, in particular, the group ingesting the test beverage (R) containing 80 mg of the pine bark extract and the group ingesting the test beverage (S) containing mg of the pine bark extract had higher values than the group ingesting the control (P).

TABLE 6

| | | Before ingestion | After ingestion | |
|---|---|---|---|---|
| Blood flow at 45 seconds after cessation of avascularization C | P (pine bark extract: 0 mg) | 7.5 ± 4.1 | 6.0 ± 3.5 | |
| | Q (pine bark extract: 40 mg) | 7.1 ± 2.9 | 6.1 ± 2.5 | # |
| | R (pine bark extract: 80 mg) | 7.7 ± 2.9 | 8.3 ± 4.2 | |

TABLE 6-continued

| | | Before ingestion | After ingestion | |
|---|---|---|---|---|
| (ml/min/100 ml tissue) | S (pine bark extract: 160 mg) | 7.5 ± 4.0 | 6.9 ± 3.4 | |
| Relative increase in arterial blood flow C/A (% FBF) | P (pine bark extract: 0 mg) | 199.6 ± 93.2 | 182.0 ± 90.6 | # |
| | Q (pine bark extract: 40 mg) | 197.7 ± 73.5 | 185.9 ± 83.6 | |
| | R (pine bark extract: 80 mg) | 207.9 ± 67.3 | 241.3 ± 90.6 | |
| | S (pine bark extract: 160 mg) | 196.8 ± 95.2 | 210.5 ± 96.6 | |

Values in the table are expressed in mean ± standard deviation.
Comparison with the group ingesting control (P)
: $p < 0.05$;
: $p < 0.01$
: $p < 0.001$ (paired t test)

Further in addition, the area under the curve (AUC) of the % FBF curve for the period ranging from zero to 60 seconds after the cessation of avascularization was computed. The results are shown in Table 7. The group ingesting the test beverage (R) containing 80 mg of the pine bark extract and the group ingesting the test beverage (S) containing 160 mg of the pine bark extract had higher values of AUC than the group ingesting the control (P).

TABLE 7

| | | Before ingestion | After ingestion | | |
|---|---|---|---|---|---|
| AUC of relative FBF curve for forearm arterial blood flow (% FBF · min) | P (pine bark extract: 0 mg) | 328.7 ± 133.2 | 319.1 ± 125.7 | | |
| | Q (pine bark extract: 40 mg) | 317.0 ± 120.6 | 305.3 ± 130.0 | ### | # |
| | R (pine bark extract: 80 mg) | 328.4 ± 94.5 | 443.1 ± 97.9 | | |
| | S (pine bark extract: 160 mg) | 294.0 ± 91.2 | 409.1 ± 176.7 | | |

Values in the table are expressed in mean ± standard deviation.
Comparison with the group ingesting control (P)
: $p < 0.05$
: $p < 0.01$
: $p < 0.001$ (paired t test)

From the foregoing results, it was suggested that an improvement in the vascular endothelial function could be achieved by continued ingestion for one week of the tea beverages to which 40 mg or more of the pine bark extract had been added; in particular, it was confirmed that the tea beverages to which 80 mg or more of the pine bark extract had been added, namely, those containing PB1 and PB3 at concentrations of 8.10 mg/L and more, had a superior vascular endothelial function improving action.

Example 2

Vascular Endothelial Function Improving Action-2 of Proanthocyanidins Containing Tea Beverages in Human Volunteers 1. Production of Proanthocyanidins Containing Tea Beverage A liquid tea extract was prepared as in Example 1 and, in accordance with the recipes shown in Table 8, a pine bark extract and L-ascorbic acid were mixed and dissolved in the liquid tea extract; thereafter, sodium bicarbonate was added to adjust the pH to 6.0. Subsequently, degassing and sterilizing treatments were performed as in Example 1 and, thereafter, the mixed solutions were filled into 350 mL PET bottles to prepare a total of three sample beverages, one control (L) and two test beverages (M, N). It was confirmed that L, M and N were indistinguishable from one another in terms of sensory stimulus (taste and aroma), appearance, and properties.

TABLE 8

| | L (control) | M | N |
|---|---|---|---|
| Liquid tea extract | | 350 mL | |
| Pine bark extract[*2] | 0 mg | 40 mg | 80 mg |
| L-ascorbic acid | | 100 mg | |

[*2]Product of TOYO SHINYAKU Co., Ltd. (Flavangenol Lot. T-0030; water extracted type)

2. Measuring PB1 and PB3 Contents

The control (L) and the test beverages (M, N) were measured for the amounts of procyanidin B1 (PB1) and procyanidin B3 (PB3) as in Example 1. The results of measurements are shown in Table 9.

TABLE 9

| | PB1 | PB3 | Total |
|---|---|---|---|
| L (pine bark extract: 0 mg) | 0 | 1.72 | 1.72 |
| M (pine bark extract: 60 mg) | 2.39 | 4.00 | 6.39 |
| N (pine bark extract: 80 mg) | 3.12 | 5.27 | 8.38 |

(Unit: mg/L)

3. Evaluating Vascular Endothelial Function by Plethysmography

Sixty-seven healthy male and female adults aged between 20 and 65 were chosen as volunteers after they gave informed prior consent to participating in the trial from ethical consideration; they satisfied either one of the following criteria, i.e., having a fasting blood glucose level of 110-139 mg/dL or a systolic blood pressure of 130-159 mmHg or a diastolic blood pressure of 85-99 mmHg in a preliminary examination conducted two weeks before the trial, or being women having menopausal symptoms (with a Kupperman index of at least 21). These volunteers were divided into three groups (n=22 or 23) and subjected to a 12-week long, double-blind test by a current control design. More specifically, the three groups of volunteers were asked to drink either the control (L) or one of test beverages (M, N) in one pack (350 mL) per day for a period of 12 weeks.

The vascular endothelial function was evaluated by plethysmography (Plethysmograph EC6, Primetech Co.) as in Example 1. Note, however, that the measurement of the vascular endothelial function was conducted a total of six times, four weeks before ingestion (pre-observation), immediately before ingestion (0 weeks), after 4, 8 and 12 weeks of ingestion, and four weeks after ingestion (post-observation).

Note here that since the healthy persons who volunteered in the present trial had initial values of the relative increase in the arterial blood flow (B/A) ranging from 166.0 to 1265.6, some of them might have been deteriorated in the vascular endothelial function. As a result of continued ingestion of the test beverages (M, N), the volunteers got their relative increase in the arterial blood flow to be within the range from 261.9 to 1417.5.

Figure 5:
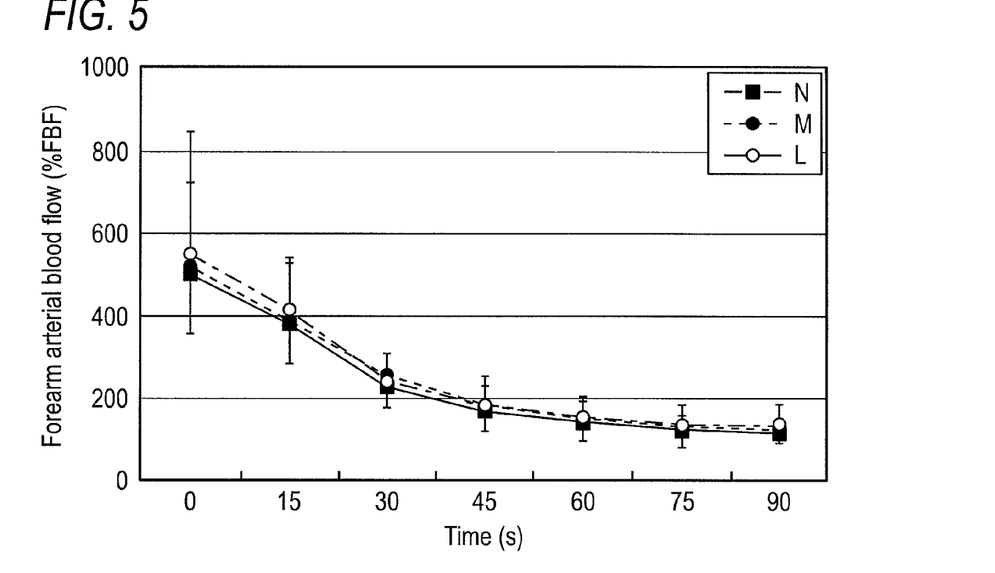
FIG. 5 is a graph showing the results of measurements of the ratio (% FBF) of the forearm arterial blood flow (FBF) after cessation of avascularization to that at rest in humans both immediately before and after 12-week ingestion of test beverages of the present invention.
Figure 6:
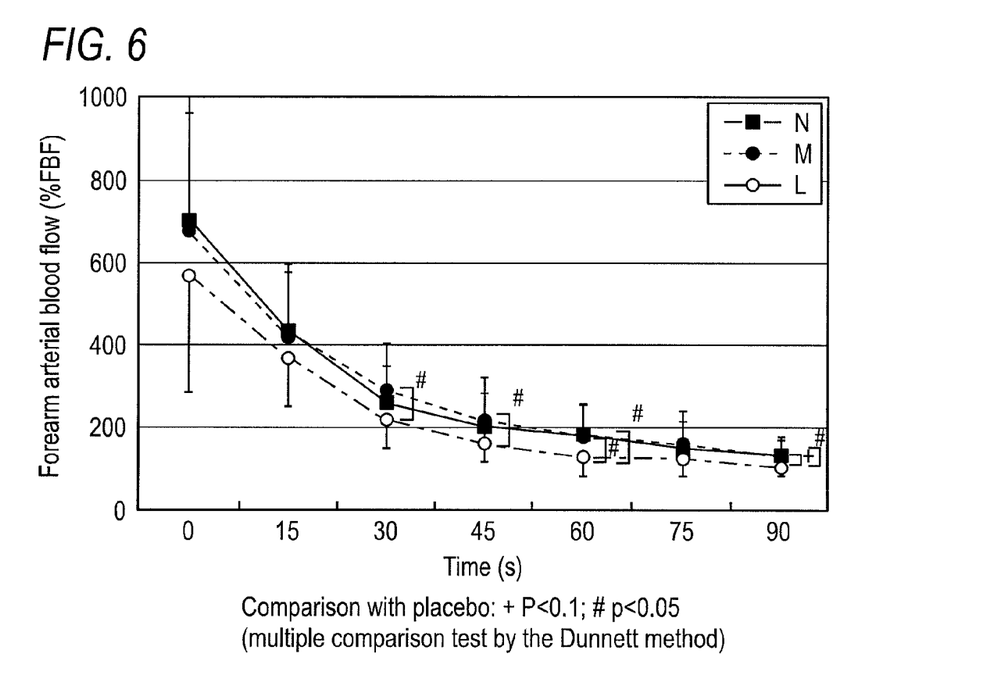
FIG. 6 is a graph showing the results of measurements of the ratio (% FBF) of the forearm arterial blood flow (FBF) after cessation of avascularization to that at rest in humans both immediately before and after 12-week ingestion of test beverages of the present invention.

FIGS. 5 and 6 show the changes with time in the percent increase of arterial blood flow (% FBF), or the reactive hyperemic arterial blood flow (forearm arterial blood flow) divided by the resting basal blood flow, that was measured both immediately before and after 12-week ingestion of the sample beverages. After 12 weeks of the ingestion, the groups ingesting the test beverages (M, N) had higher values than the group ingesting the control (L) at any of the points in time between 0 and 90 seconds after the cessation of avascularization.

Table 10 shows the changes in the relative increase in arterial blood flow (C/A) (% FBF) where C is the blood flow at 45 seconds after the cessation of avascularization, as compared with the resting basal blood flow (resting forearm arterial blood flow) (the upper row shows the values of actual measurement; the lower row shows the amounts of changes (Δ values) from the value at the time immediately before ingestion). Each of the groups ingesting the test beverages (M, N) had higher values of the relative increase in arterial blood flow (C/A) than the group ingesting the control (L). The effectiveness in the groups ingesting the test beverages (M, N) was also apparent from the great differences in Δ value from the group ingesting the control (L).

Table 11 shows the changes in the area under the curve of the % FBF curve for the period from zero to 60 seconds after the cessation of avascularization (the upper row shows the values of actual measurement; the lower row shows the amounts of changes (Δ values) from the value at the time immediately before ingestion). During the ingestion for more than four weeks, each of the groups ingesting the test beverages (M, N) had higher values of AUC than the group ingesting the control (L). The effectiveness in the groups ingesting the test beverages (M, N) was also apparent from the great differences in Δ value from the group ingesting the control (L).

TABLE 10

| | Group of sample beverages | Pre-observation period | Immediately before ingestion | After 4 weeks of ingestion | After 8 weeks of ingestion | |
|---|---|---|---|---|---|---|
| Forearm arterial blood flow at 45 seconds after cessation of avascularization C (mL/min/100 mL tissue)/A (% FBF) | L (pine bark extract: 0 mg) | 188.7 ± 74.2 | 184.3 ± 67.0 | 164.6 ± 55.7 | 163.6 ± 54.7 | ## |
| | M (pine bark extract: 60 mg) | 191.9 ± 57.5 | 179.5 ± 57.7 | 203.1 ± 67.3 + | 247.5 ± 123.3 | |
| | N (pine bark extract: 80 mg) | 205.9 ± 93.1 | 166.6 ± 63.5 | 174.2 ± 59.1 | 177.2 ± 74.8 | |
| ΔC/A (% FBF) | L (pine bark extract: 0 mg) | 4.4 ± 81.5 | 0.0 ± 0.0 | −19.7 ± 86.7 | −20.7 ± 56.1 | ## |
| | M (pine bark extract: 60 mg) | 12.4 ± 60.6 | 0.0 ± 0.0 | 23.6 ± 65.5 | 66.0 ± 112.0 | |
| | N (pine bark extract: 80 mg) | 38.4 ± 114.1 | 0.0 ± 0.0 | 7.6 ± 70.6 | 10.6 ± 81.9 | |

| | Group of sample beverages | After 12 weeks of ingestion | Post-observation period | |
|---|---|---|---|---|
| Forearm arterial blood flow at 45 seconds after cessation of avascularization C (mL/min/100 mL tissue)/A (% FBF) | L (pine bark extract: 0 mg) | 159.1 ± 44.9 | 161.3 ± 48.5 | |
| | M (pine bark extract: 60 mg) | 213.8 ± 103.4 # | 194.8 ± 71.7 | |
| | N (pine bark extract: 80 mg) | 199.3 ± 80.0 | 174.9 ± 66.3 | |
| ΔC/A (% FBF) | L (pine bark extract: 0 mg) | −25.2 ± 65.2 | −23.0 ± 67.3 | |
| | M (pine bark extract: 60 mg) | 34.3 ± 92.5 # | 15.4 ± 89.6 | # |
| | N (pine bark extract: 80 mg) | 32.6 ± 84.4 | 14.8 ± 89.9 | |

Values are mean ± standard deviation.
Inter-group comparison:
+ $p < 0.1$;
$p < 0.05$;
$p < 0.01$ (multiple comparison test by the Dunnett method)

TABLE 11

| | Group of sample beverages | Pre-observation period | Immediately before ingestion | After 4 weeks of ingestion | | After 8 weeks of ingestion | |
|---|---|---|---|---|---|---|---|
| AUC of the relative FBF curve for forearm arterial blood flow (% FBF · min) | L (pine bark extract: 0 mg) | 312.7 ± 101.5 | 297.5 ± 88.2 | 283.0 ± 81.8 | } # | 278.0 ± 96.9 | } + |
| | M (pine bark extract: 60 mg) | 289.1 ± 64.3 | 289.2 ± 61.8 | 336.9 ± 69.9 | | 346.2 ± 120.6 | |
| | N (pine bark extract: 80 mg) | 296.3 ± 105.3 | 273.4 ± 89.2 | 282.8 ± 72.5 | | 300.3 ± 85.9 | |
| ΔAUC of the relative FBF curve for forearm arterial blood flow (% FBR · min) | L (pine bark extract: 0 mg) | 15.2 ± 104.4 | 0.0 ± 0.0 | −14.5 ± 111.8 | } + | −19.4 ± 103.3 | } + |
| | M (pine bark extract: 60 mg) | −0.1 ± 67.3 | 0.0 ± 0.0 | 47.8 ± 90.2 | | 55.0 ± 113.2 | |
| | N (pine bark extract: 80 mg) | 22.9 ± 124.7 | 0.0 ± 0.0 | 9.4 ± 89.6 | | 27.0 ± 109.9 | |

| | Group of sample beverages | After 12 weeks of ingestion | | Post-observation period |
|---|---|---|---|---|
| AUC of the relative FBF curve for forearm arterial blood flow (% FBF · min) | L (pine bark extract: 0 mg) | 272.1 ± 83.2 | } + } + | 278.7 ± 80.0 |
| | M (pine bark extract: 60 mg) | 338.8 ± 118.0 | | 311.0 ± 99.0 |
| | N (pine bark extract: 80 mg) | 332.4 ± 104.0 | | 303.3 ± 88.6 |
| ΔAUC of the relative FBF curve for forearm arterial blood flow (% FBR · min) | L (pine bark extract: 0 mg) | −25.4 ± 102.9 | } # } # | −18.8 ± 127.4 |
| | M (pine bark extract: 60 mg) | 49.7 ± 94.6 | | 21.8 ± 89.4 |
| | N (pine bark extract: 80 mg) | 59.0 ± 101.5 | | 38.0 ± 140.3 |

Values are mean ± standard deviation.
Inter-group comparison:
+ p < 0.1;
# p < 0.05;
## p < 0.01 (multiple comparison test by the Dunnett method)

From the foregoing results, it was suggested that the tea beverages to which 60 mg or more of the pine bark extract had been added, namely, those containing PB1 and PB3 at total concentrations of 6.39 mg/L and more, caused an increase in blood flow when they were ingested continuously. In particular, as shown in FIG. 6, not only the maximum forearm arterial blood flow but also the blood flow up until 90 seconds after the cessation of avascularization was increased by continued ingestion of the tea beverages to which 60 mg or more of the pine bark extract had been added and this would suggest a great improvement in the vascular endothelial function.

4. Evaluating the Vascular Endothelial Function by Biochemical Examination of Blood A hematological test was conducted four weeks before ingestion (pre-observation), immediately before ingestion (0 weeks), after 4, 8 and 12 weeks of ingestion, and four weeks after ingestion (post-observation) and the blood NOx level (the sum of $NO_2^-$ and $NO_3^-$) was analyzed. In addition, the urinary 8-OHdG level was measured both immediately before and after 12 weeks of ingestion.

Table 12 shows the changes in the blood NOx level (μM). The group ingesting the control (L) experienced no variations by sample beverage; however, in each of the groups ingesting the test beverages (M, N), the NOx level became higher than it was immediately before ingestion and the increase grew as the period of ingestion prolonged. In particular, the group ingesting the tea beverage (N) to which 80 mg of the pine bark extract had been added had a significantly higher value of NOx than the group ingesting the control (L). From these results, it was suggested that a NO-dependent improvement in the vascular endothelial function would be achieved by continued ingestion of the tea beverages to which 60 mg or more of the pine bark extract had been added, namely, those containing PB1 and PB3 at total concentrations of 6.39 mg/L and more.

TABLE 12

| | Group of sample beverages | Pre-observation period | Immediately before ingestion | After 4 weeks of ingestion | | After 8 weeks of ingestion | After 12 weeks of ingestion | | Post-observation period |
|---|---|---|---|---|---|---|---|---|---|
| AUC of the relative FBF curve for forearm | L (pine bark extract: 0 mg) | 17.4 ± 12.3 | 30.2 ± 34.7 | 20.2 ± 12.4 | } + | 17.2 ± 9.4 | 21.3 ± 12.3 | } # } + | 30.3 ± 22.0 |
| | M (pine bark extract: 60 mg) | 20.3 ± 10.9 | 17.1 ± 8.2 | 17.5 ± 8.2 | | 19.4 ± 10.7 | 23.7 ± 12.3 | | 25.6 ± 14.5 |

TABLE 12-continued

| Group of sample beverages | | Pre-observation period | Immediately before ingestion | After 4 weeks of ingestion | After 8 weeks of ingestion | After 12 weeks of ingestion | Post-observation period |
|---|---|---|---|---|---|---|---|
| arterial blood flow (% FBF · min) | N (pine bark extract: 80 mg) | 18.4 ± 9.2 | 21.3 ± 12.2 | 14.2 ± 5.7 | 25.4 ± 20.8 | 31.0 ± 15.2 | 25.9 ± 14.5 |

Values are mean ± standard deviation.
Inter-group comparison:
+ p < 0.1;
# p < 0.05; (multiple comparison test by the Dunnett method)
Comparison with "immediately before ingestion":
+ p < 0.1;
# p < 0.05;
## p < 0.01;
### p < 0.001 (multiple comparison test by the Bonferroni method)

Table 13 shows the changes in the urinary 8-OHdG level (mg/mL). In each of the groups ingesting the sample beverages (L, M, N), the urinary 8-OHdG level decreased as the result of 12-week beverage ingestion; in particular, the group ingesting the tea beverage (N) to which 80 mg of the pine bark extract had been added had a significantly lower value of 8-OHdG than the value at the time immediately before ingestion. From this fact, it became clear that continued ingestion of tea beverages reduced oxidation stress disorder and that particularly by continued ingestion of the tea beverage to which 80 mg of the pine bark extract had been added, namely, the one containing PB1 and PB3 at a total concentration of at least 8.1 mg/L, oxidation stress disorder was reduced.

TABLE 13

| Group of sample beverages | Immediately before ingestion | After 12 weeks of ingestion |
|---|---|---|
| L (pine bark extract: 0 mg) | 8.5 ± 3.6 | 7.8 ± 3.7 |
| M (pine bark extract: 60 mg) | 8.5 ± 4.0 | 7.9 ± 4.5 |
| N (pine bark extract: 80 mg) | 10.7 ± 6.2 | 7.3 ± 4.2* |

Values are mean ± standard deviation.
Comparison with "immediately before ingestion": *p < 0.05 (paired t test)

Example 3

Organoleptic Evaluation Test-1

Green tea (8 kg) was put into 300 L of hot water with 80° C. and extracted at the same temperature for 5 minutes. The resulting liquid extract was cooled and centrifuged; a clear supernatant was recovered as a green tea extract. The pH of the liquid extract was adjusted to about 6.0 using sodium bicarbonate and vitamin C; then, a hot-water extracted pine bark extract (Flavangenol of TOYO SHINYAKU Co., Ltd.; Lot. T-0030) was added such that it would be contained in the final composition (350 mL) in amounts of 0, 40, 60, 80, 100, 125, 150, 175, 200, 250, and 300 mg; pure water was added to give a final volume of 1000 L. Soon after their production, the samples were drunk by eight panelists (3 males and 5 females) who were asked to evaluate their taste and aroma as Flavangenol-containing green tea beverages. The eight panelists were asked to grade the preference of the beverages by the criteria specified below and the scores they gave were added up. The contents of PB1 and PB3 in the sample beverages were determined as in Example 1.

The results of the organoleptic evaluation are shown in Table 14, and the results of measurement of PB1 and PB3 in Table 15. As it turned out, the tea beverages containing 0-200 mg, preferably 0-125 mg, of the pine bark per 350 mL, namely, those tea beverages which contained PB1 and PB3 at a total concentration of no more than 30 mg/L, preferably no more than 20 mg/L, were less pungent and free of any peculiar flavor to become easier to drink.

(Criteria for evaluation)

| Best preferred: | 5 |
|---|---|
| Preferred: | 4 |
| Moderate: | 3 |
| Less preferred: | 2 |
| Not preferred: | 1 |

TABLE 14

| Amount of Flavangenol added (mg/350 ml) | Panelists | | | | | | | | Total score |
|---|---|---|---|---|---|---|---|---|---|
| | A | B | C | D | E | F | G | H | |
| 0 | 5 | 5 | 5 | 5 | 4 | 3 | 3 | 5 | 35 |
| 40 | 4 | 5 | 5 | 5 | 4 | 5 | 5 | 5 | 38 |
| 60 | 4 | 4 | 5 | 5 | 4 | 4 | 4 | 5 | 35 |
| 80 | 4 | 4 | 5 | 5 | 4 | 4 | 4 | 4 | 34 |
| 100 | 3 | 4 | 5 | 5 | 3 | 4 | 3 | 4 | 31 |
| 125 | 3 | 3 | 4 | 5 | 3 | 3 | 3 | 4 | 28 |
| 150 | 2 | 3 | 3 | 5 | 2 | 3 | 2 | 3 | 23 |
| 175 | 2 | 3 | 2 | 5 | 2 | 2 | 2 | 3 | 21 |
| 200 | 2 | 3 | 2 | 4 | 2 | 2 | 2 | 3 | 20 |
| 250 | 1 | 2 | 1 | 2 | 1 | 1 | 1 | 2 | 11 |
| 300 | 1 | 1 | 1 | 1 | 1 | 1 | 1 | 1 | 8 |

TABLE 15

Unit (mg/L)

| Amount of pine bark extract added | PB1 | PB3 | Total |
|---|---|---|---|
| 0 | 0 | 2.43 | 2.43 |
| 40 | 3.24 | 4.61 | 7.85 |
| 60 | 5.06 | 5.82 | 10.88 |
| 80 | 7.03 | 6.74 | 13.77 |
| 100 | 8.55 | 7.85 | 16.40 |
| 125 | 10.13 | 9.24 | 19.37 |
| 200 | 16.20 | 13.33 | 29.53 |
| 250 | 20.25 | 16.06 | 36.31 |
| 300 | 24.30 | 18.78 | 43.08 |

Example 4

Organoleptic Evaluation Test-2

Green tea (8 kg) was put into 300 L of hot water with 80° C. and extracted at the same temperature for 5 minutes. The resulting liquid extract was cooled and centrifuged; a clear supernatant was recovered as a green tea extract. The pH of the liquid extract was adjusted to about 6.0 using sodium bicarbonate and vitamin C; then, a hot-water extracted type of pine bark extract, Flavangenol (TOYO SHINYAKU Co., Ltd.; T-27 of Lot. T-0030) or a hydrous-ethanol extracted type of pine bark extract, Pycnogenol (product of Nihon Siber Hegner K. K.; L F830 of Lot. F-830) was added such that either would be contained in the final composition (350 mL) in an amount of 80 mg; pure water was added to give a final volume of 1000 L. Soon after their production, the samples were drunk by eight panelists (3 males and 5 females) who were asked to evaluate their taste and aroma. The features to be evaluated were the same as in Example 3. In addition, the pine bark extracts were subjected to compositional analysis as in Test 1. A compositional analysis was also made for another hydrous-ethanol extracted type of pine bark extract, Flavangenol (TOYO SHINYAKU Co., Ltd.; P-15 of Lot. T-0015), as a comparison.

The results of the organoleptic evaluation are shown in Table 16 and the results of compositional analyses in Table 17; in addition, the concentration of ferulic acid in PP and that of dihydroquercetin in DHF are shown in Table 18. As is clear from Table 16, the tea beverage containing the pine bark extract of hot-water extracted type was less pungent and free of any peculiar flavor to become easier to drink than the tea beverage containing the pine bark extract of hydrous-ethanol extracted type. From Table 17, it has been found that the extract with hot water contained PP and DHF in extremely small amounts compared to the extract with hydrous ethanol. From Table 18, it may well be said preferable to use a pine bark extract containing ferulic acid and dihydroquercetin in a total amount of 10 µg/mg, preferably 5 µg/mg, as an index.

| (Criteria for evaluation) | |
|---|---|
| Best preferred: | 5 |
| Preferred: | 4 |
| Moderate: | 3 |
| Less preferred: | 2 |
| Not preferred: | 1 |

TABLE 16

| | Panelists | | | | | | | | Total score |
|---|---|---|---|---|---|---|---|---|---|
| | A | B | C | D | E | F | G | H | |
| Flavangenol containing green tea | 4 | 4 | 5 | 5 | 4 | 4 | 4 | 4 | 34 |
| Pycnogenol containing green tea | 2 | 3 | 3 | 1 | 2 | 3 | 2 | 1 | 17 |

TABLE 17

| | | C + EC | Pr | PP | DHF | Others |
|---|---|---|---|---|---|---|
| | | | | | | (Unit: wt %) |
| T-27 | Extract with hot water | 6 | 60 | 0.5 | 0.5 | 33 |
| P-15 | Extract with hydrous ethanol | 5 | 45 | 10 | 2 | 38 |
| F830 | Extract with hydrous ethanol | 3 | 48 | 6 | 4 | 39 |

TABLE 18

| | | Ferulic acid µg/mg | Dihydroquercetin µg/mg |
|---|---|---|---|
| T-27 | Extract with hot water | 1.664 | 1.468 |
| P-15 | Extract with hydrous ethanol | 9.382 | 2.308 |
| F830 | Extract with hydrous ethanol | 5.74 | 30.77 |

The invention claimed is:

1. A tea beverage for improving vascular endothelial function comprising effective amounts of a liquid *Camellia sinensis* extract, procyanidin B1 (PB1) represented by formula (I):

[Formula 1]

and procyanidin B3 (PB3) represented by formula (II):

[Formula 2]

with the sum of the procyanidins being at least 6.4 mg/L, wherein the PB1 and PB3 are contained in a pine bark extract;

wherein the pine bark extract is obtained by extracting pine bark with water having a temperature of 70-100° C., and wherein the tea beverage further comprises ascorbic acid, sodium ascorbate, and/or sodium hydrogen carbonate.

2. A tea beverage according to claim 1, wherein the tea beverage is in a container.

3. The tea beverage according to claim 1, further comprising an antioxidant.

4. The tea beverage according to claim 1, wherein said pine bark extract comprises ferulic acid and dihydroquercetin, and the sum of their contents is equal to or less than 10 µg/mg.

5. The tea beverage according to claim 1, wherein said liquid *Camellia sinensis* extract comprises a green tea extract.

6. A process for preparing the tea beverage of claim 1, which comprises:
   blending the liquid *Camellia sinensis* extract with the pine bark extract, wherein the pine bark extract is extracted with water having the temperature of 70-100° C.

7. The process according to claim 6, wherein said pine bark extract further comprises ferulic acid and dihydroquercetin, and the sum of their contents is equal to or less than 10 µg/mg.

8. The process according to claim 6, further comprising sterilizing the blended mixture and filling the sterilized mixture into a container.

9. A method for improving vascular endothelial function, comprising administering an effective amount of the tea beverage according to claim 1 to a subject in need thereof.

10. The method according to claim 9, wherein the tea beverage is administered continuously for 1-12 weeks at a daily dose of 350 ml.

11. The method according to claim 9, wherein the tea beverage is administered to a human having a maximum value of a relative increase in arterial blood flow of 0-400.

12. The method according to claim 9, wherein the blood flow of the subject is improved.

* * * * *